United States Patent [19]

Kanner et al.

[11] Patent Number: 5,634,910
[45] Date of Patent: Jun. 3, 1997

[54] SYRINGE INSTRUMENT

[75] Inventors: Rowland W. Kanner; Richard M. Davis, both of Guntersville; Richard Rabenau, Birmingham, all of Ala.

[73] Assignee: Ryder International Corporation, Arab, Ala.

[21] Appl. No.: 532,334

[22] Filed: Sep. 22, 1995

[51] Int. Cl.$^6$ ............................................ A61M 5/00
[52] U.S. Cl. .................................. 604/208; 604/210
[58] Field of Search ........................... 604/191–194, 604/121, 218, 228, 208, 224, 209, 118, 123–124

[56] References Cited

U.S. PATENT DOCUMENTS

| | | |
|---|---|---|
| 4,583,974 | 4/1986 | Kokernak . |
| 4,743,230 | 5/1988 | Nordquest . |
| 4,838,864 | 6/1989 | Peterson . |
| 4,929,238 | 5/1990 | Baum . |
| 5,168,757 | 12/1992 | Rabenau et al. . |
| 5,306,248 | 4/1994 | Barrington . |
| 5,318,534 | 6/1994 | Williams et al. . |

FOREIGN PATENT DOCUMENTS 8909071   10/1989   WIPO .

*Primary Examiner*—Robert A. Hafer
*Assistant Examiner*—Perry E. Van Over

*Attorney, Agent, or Firm*—Trexler, Bushnell, Giangiorgi & Blackstone, Ltd.

[57] ABSTRACT

A syringe instrument for particular use in medical balloon inflation procedures comprises a fluid chamber and a plunger arranged to displace fluid from the chamber for delivery to inflate the balloon, and incorporates control structure arranged to provide a series of releasible space limits for respective displacements of the plunger within the chamber. The control structure allows the fluid in the chamber to be pressurized at selective predetermined pressure levels governed by the releasable limits for the plunger displacements. A reverse drive structure is provided for reverse-displacement of the plunger from the fluid chamber to enable self-aspiration of fluid into the chamber from the balloon in order to simplify balloon deflation and removal from the patient. The reverse drive structure is manually activated with the same hand which depresses the plunger, for single handed operation of both the forward and reverse plunger motions. A second fluid displacement structure separate from the plunger, is reversibly displaceable into and from the chamber in order to enable charging aspiration of the pressure fluid into the chamber. A pressure balance mechanism is provided cooperating to allow the plunger to self-adjust in order to maintain the proper predetermined balloon pressure as the dilating duct induces increase in the balloon volume.

24 Claims, 4 Drawing Sheets

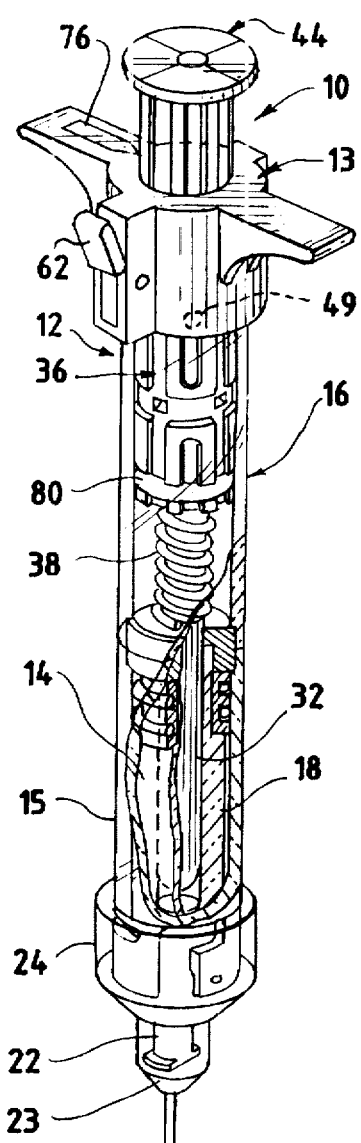

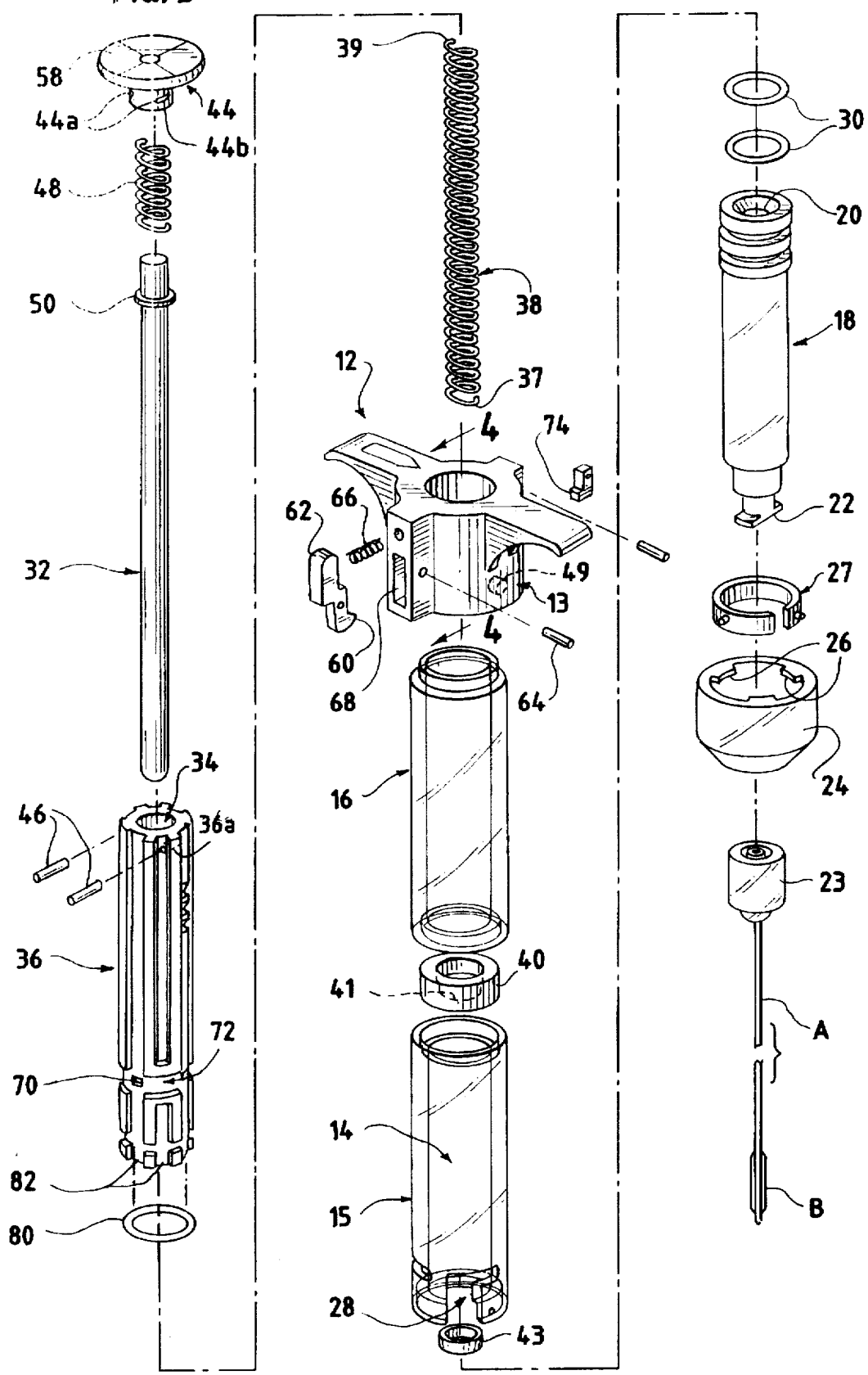

SYRINGE INSTRUMENT

BACKGROUND

This invention relates to syringe instruments for fluid pressure control and more particularly relates to syringe instruments employed for medical catheter balloon inflation procedures.

Treatment of obstructed nasal lacrimal (tear) ducts in both adult and pediatric procedures has been developed from coronary balloon angioplasty, in which a small balloon catheter is inserted into the duct and then inflated to dilate the duct and eliminate obstruction. Current lacrimal duct dilation treatment requires the use of a standard syringe without pressure indication inflation but also requires a second syringe for aspirating and deflating the balloon for removal. Although typical coronary angioplasty inflators have been adapted for lacrimal duct balloon treatment in place of standard syringes, the bulkier angioplasty syringe generally requires two-handed operation to pressurize and aspirate in the balloon treatment. These disadvantages are eliminated in the improved syringe instruments in accordance with the present invention.

SUMMARY OF THE INVENTION

In accordance with the present invention, a syringe instrument for particular use in medical balloon inflation procedures comprises a fluid chamber and a plunger arranged to displace fluid from the chamber for delivery to inflate the balloon, and incorporates control structure arranged to provide a series of releasible space limits for respective displacements of the plunger within the chamber. The control structure allows the fluid in the chamber to be pressurized at selective predetermined pressure levels governed by the releasable limits for the plunger displacements. A reverse drive structure is provided for reverse-displacement of the plunger from the fluid chamber to enable self-aspiration of fluid into the chamber from the balloon in order to simplify balloon deflation and removal from the patient. The reverse drive structure is manually activated with the same hand which depresses the plunger, for single handed operation of both the forward and reverse plunger motions.

In another aspect of the invention, a second fluid displacement structure separate from the plunger, is reversibly displaceable into and from the chamber in order to enable charging aspiration of the pressure fluid into the chamber. In another aspect of the invention, a pressure balance mechanism is provided cooperating to allow the plunger to self-adjust in order to maintain the proper predetermined balloon pressure as the dilating duct induces increase in the balloon volume.

In a preferred embodiment, according to the invention, the control structure includes a plurality of stop formations in serial arrangement coupled to the plunger and a latch member releasibly engageable with each said stop formation to define said plunger displacement limits. The reverse drive structure includes a return spring which is compressed with forward displacement of the plunger and is selectively activated by withdrawal of the catch member from a stop formation to enable the reverse displacement of the plunger. A piston separate from the plunger is reciprocated within the fluid chamber for volume expansion thereof to induce aspirating charge of the pressurizing fluid into the chamber. The piston includes a bore which receives the plunger in telescopic arrangement to produce high pressured fluid displacement from the chamber. A stationary fluid seal is arranged on the fluid chamber for travel of the plunger therethrough so that the plunger need not carry a dynamic sealing element and the plunger can displace fluid from the piston bore without need for fluid seal therebetween.

BRIEF DESCRIPTION OF THE DRAWINGS

FIG. 1 is a perspective view of one embodiment of a syringe instrument in accordance with the invention;

FIG. 2 is an enlarged, perspective view of an internal control sleeve and a plunger cap of the syringe instrument shown in FIG. 1;

FIG. 3 is a perspective view similar to FIG. 2, in which the control sleeve has been rotated to illustrate selective, plunger displacement stop structure;

FIG. 4 is an enlarged, sectional view along a plane indicated by line 4—4 in FIG. 5;

FIG. 5 is an exploded, perspective view of the syringe instrument shown in FIG. 1;

DETAILED DESCRIPTION OF THE PREFERRED EMBODIMENT

Figure 6:
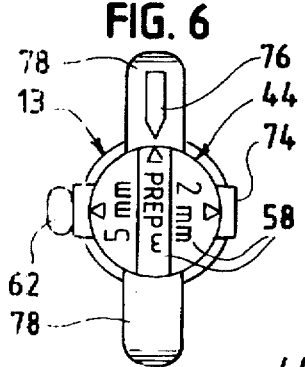
FIG. 6 is a top plan view of the plunger cap similar to FIG. 4 showing one of a plurality of plunger displacement control selections with corresponding indicia on the plunger cap.
Figure 8:
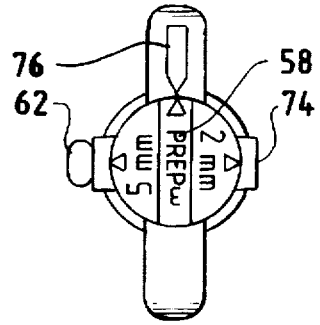
FIGS. 8 and 9 are cap and syringe views similar to FIGS. 6 and 7 showing retraction of a piston structure relative to the extended piston position shown in FIG. 7.

Referring to FIGS. 1 and 5, an embodiment of the inflator device in accordance with the present invention is designated generally by reference character 10. The inflator device 10 has a generally cylindrical barrel 12 housing a fluid displacement chamber 14 interiorly arranged within a forward portion 15 and provided with a control mechanism portion generally designated 16 arranged at the rearward portion of the barrel 12. Barrel portions 15 and 16 can be integrally molded. A reciprocally moveable piston structure 18 is slidably received and projectable from the fluid chamber 14 to enable aspiration of pressurizing fluid into the chamber by fluid communication through a conduit bore 20 (FIG. 3) formed through the piston 18. The projecting end of the piston 18 has an integral fluid tube coupler 22, for example a Lure® lock fitting, for coupling to a mating delivery tube coupler 23 connected to the tubular lead, A, for example to a catheter and balloon B which may have been previously placed in patient's lacrimal duct, as described hereinafter. The piston has an externally secured cap 24 provided with locking tongues 26 which are twisted into slots 28 formed adjacent the end of the forward barrel portion 15 to provide bayonet locking of the piston 18 withdrawn into the fluid displacement chamber 14. The piston 18 carries a pair of spaced O-rings 30 to seal against the chamber wall. A retainer ring 27 is fired into the end of the chamber 14 to stop the piston 18 at maximum projection from the chamber as in FIG. 7.

Figure 9:
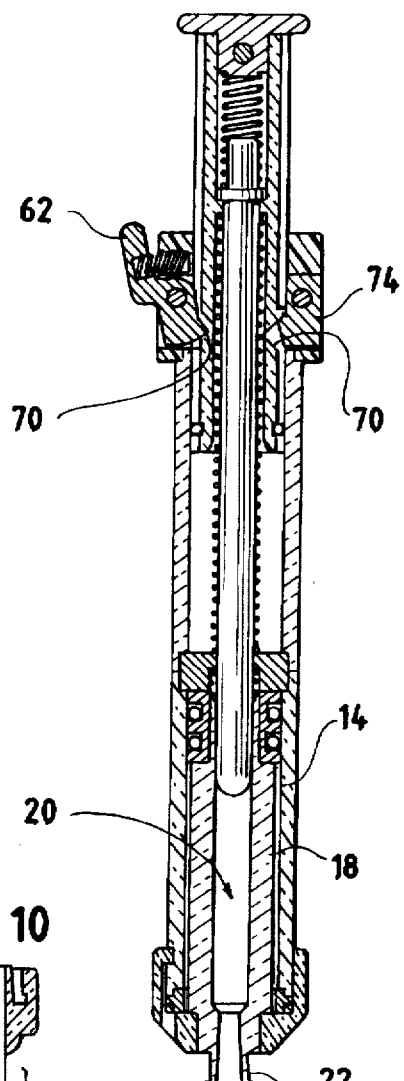
Figure 10:
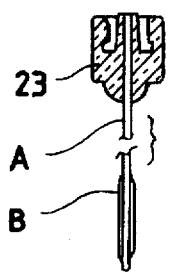
FIG. 10 is a sectional view of an inflatable balloon and fluid coupler connectable to the piston structure shown in FIGS. 7 and 9.
Figure 11:
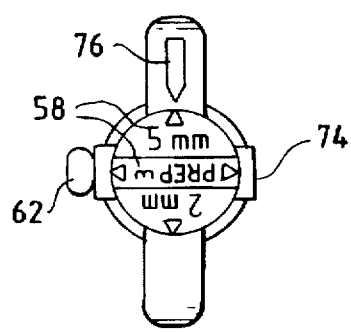
FIG. 11 is a top plan view of the plunger cap shown in FIGS. 6 and 8, in which the cap has been rotated for selective plunger displacement operation control of the syringe instrument.
Figure 12:
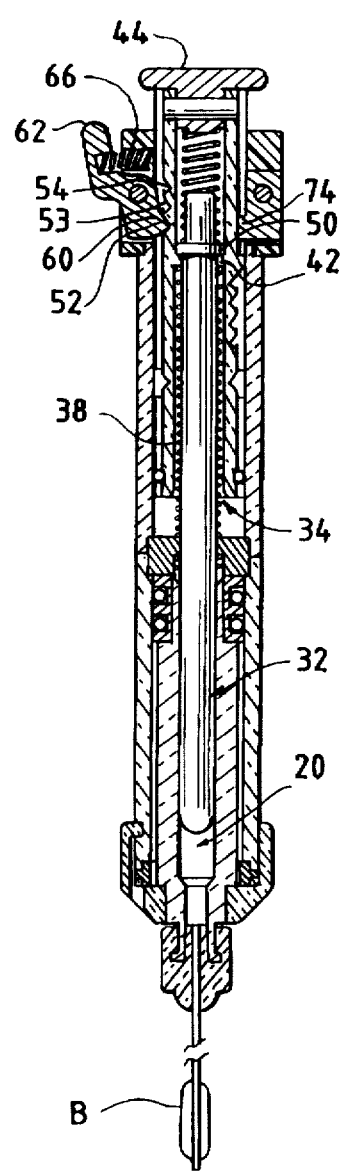
FIG. 12 is a sectional view similar to FIGS. 7 and 9, showing sequential operation and plunger displacement and corresponding progressive inflation of the connected balloon.

As best shown in FIGS. 5 and 9, an elongate fluid plunger 32 fits through the central bore 34 of a control sleeve structure 36. The plunger 32 projects from the sleeve structure 36 into the fluid displacement chamber 14 as shown in FIG. 12 and is received within the smaller bore 20 of the retracted piston 18. A plunger return spring 38 has a stationary end 37 secured to a spring seat 40 and annular gland joining the forward barrel portion 15 to the rearward barrel portion 16. The annular gland 40, together with gland 43, also seats a stationary or "static" O-ring seal 41 which seals the travel of the plunger 32 therethrough and facilitates entry and exit of the plunger through the piston bore 20, eliminating need for the plunger to carry any dynamic "O-ring" for fluid sealing. The moveable spring end 39 extends through the sleeve bore 34 surrounding the plunger 32 and bears against an internal annular spring seat 42 formed within the sleeve structure 36. Spring 38 provides rearward (return) biasing force on the sleeve 36 (and plunger 32).

The projecting end of the sleeve 36 carries a thumb cap 44 secured by pins 46 and respective nested sleeve holes and cap grooves 36a and 44a.

Figure 7:
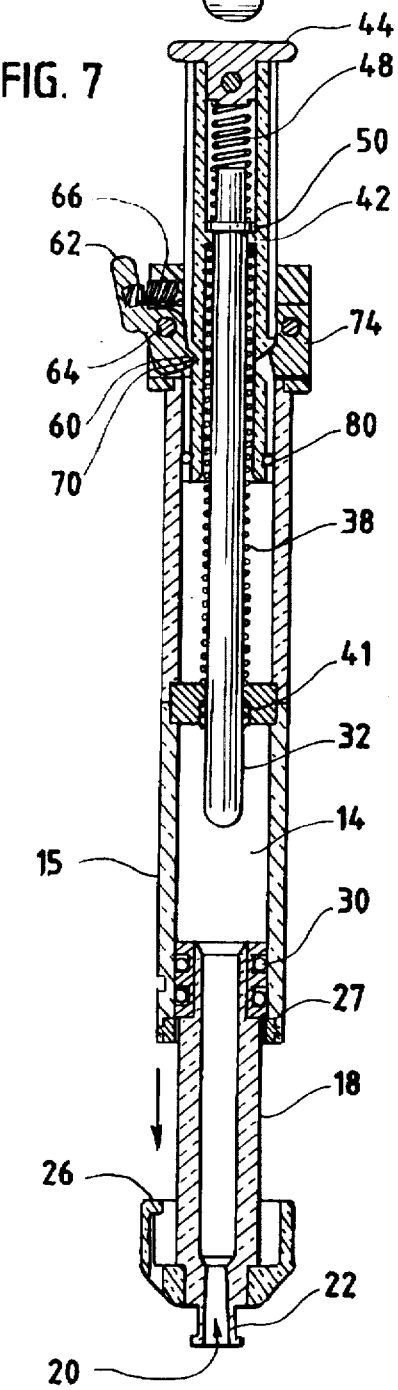
FIG. 7 is a longitudinal sectional view of the syringe instrument shown in FIG. 1.

As best shown in FIG. 7, the bottom surface 44b of the cap 44 is a seat for the rearward end of an accumulator, or pressure balancing spring 48 whose forward end bears on an annular flange 50 formed on the plunger 32 to provide preload pressure on the plunger 32 as well as a pressure balance with respect to the fluid chamber pressure as further described hereinafter. The plunger flange 50 is normally engaged against the rearward surface of the internal sleeve wall 42, and this engagement transmits rearward force from the return spring 38 to the plunger 32.

Referring again to FIGS. 2 and 3, the control sleeve structure 36 and cap 44 together carry the plunger 32 through a series of selective displacements in order to pressurize the fluid in the chamber 14 at selective predetermined pressure levels governed by the limited plunger displacements. In the illustrated embodiment, the control sleeve structure 36 is provided with detent, stop formations in the form of serial arrangement of longitudinally spaced notches 52,53,54 formed into a longitudinal groove 56 (which is indicated by a radial indicia 58 on the top of the cap 44 as further described hereinafter). Each of the notches 52,53,54 is separately alignable to receive a catch hook 60 on the end of a lever 62 pivotally mounted on the control collar 13 secured at the end of the rearward control portion 16 of the housing 12. The lever 62 pivots on a pin 64 with a biasing spring 66 which releasably urges the catch hook 60 radially inwardly through access slot 68 into engagement with the groove 56 and retention in one of the stop notches 52,53,54 corresponding with a selective longitudinal sleeve and plunger displacement enabling incremental balloon inflation as more fully described hereinafter.

Referring again to FIGS. 2 and 3, in the illustrated embodiment, the control sleeve structure 36 is provided with four longitudinal operating grooves 55,56,57 and 59 which are radially spaced for example 90° apart. Three longitudinal clearance grooves 51,151,251 are arranged at 45° radial spacing between respective grooves 56,57,59 and 55. The clearance grooves 51,151,251 allow sleeve travel clearance relative to a travel stop pin 49 projecting thereinto from the control collar 13 as shown in FIGS. 1–4 and 4 and further described hereinafter.

Each of the grooves 55,56,57 and 59 has a most forwardly positioned notch 70 which notches 70 are formed within a radially circumferential groove 72 which intersects the longitudinal grooves 55,56,57 and 59. The radial groove 72 serves as the longitudinal location of the sleeve 36 at which a rotational selection can be made among the longitudinal, operating grooves since a fixed inwardly projecting guide 74 is received within a respective operating groove located 180° in opposition to the groove aligned with the catch hook 60. The projection of the guide 74 into a respective longitudinal groove not only forms a guide lock to maintain the correct longitudinal operating groove alignment with the hook 60 but also locks the entire sleeve 36 against radial rotation and groove selection except when the sleeve 36 is longitudinally displaced to align the radial groove 72 with the guide and rotation lock 74 which alignment allows rotative clearance of the projecting guide 74 and travel stop pin 49 received therein. During such rotative groove selection from among the longitudinal grooves, the operator's finger will pivot the latch hook 60 radially outwardly to remove the hook 60 from the previously selected terminal notch 70 governing the longitudinal groove selection from among 55,56,57 and 59 to establish the rotative clearance of the radial groove 72 with respect to the hook 60. Thereafter, when the selected operating groove is radially aligned with the latch hook 60 as indicated by the corresponding indicia alignment with the arrow 76, removal of the operator's finger from the lever 62 will allow the pivotally inward engagement of the latch hook 60 into the terminal notch 70 of the selected operating groove to lock the selection and prevent any further rotation of the sleeve structure 36.

Each of the longitudinal grooves 55,56,57 and 59 has a different spacial arrangement of notches therealong, for example, while longitudinal groove 56 is provided with three such notches 52,53 and 54 for example representing plunger displacements corresponding to differential fluid pressure and balloon inflations in representative range between 2–8 atmospheres of fluid pressure, grooves 57 and 59 can have respective notch spacing and arrangement 57a, 57b and 57c and 59a, 59b and 59c for reception of the latch hook 60 at different incremental sleeve and plunger displacements. The selectivity between different plunger displacements and corresponding differential fluid pressures enables proper inflation of variable balloon dimensions selectively corresponding to the range of lacrimal duct dimensions from infant to adult patients. The travel stop pin 49 cooperates with appropriately correlated location of a stop formation in each clearance groove, for example stop 152 in groove 151 (FIG. 3), to prevent plunger travel advance beyond the respective terminal notch, e.g. 57c, and thereby prevent any balloon inflation in excess of the corresponding maximum pressure.

In operation of the syringe instrument 10 to inflate a balloon B already placed in the patient's lacrimal duct, the latch lever 62 is manually pivoted to allow longitudinal adjustment of the plunger sleeve 36 to bring the circumferential groove 72 into alignment with the foot of the guide 74 allowing rotation of the plunger cap 44 to bring the "prep" indicia into alignment position with the pointer 76 on the finger flange 78 of the control collar 13 as shown in FIGS. 6 and 7. The resulting longitudinal position will be locked by the travel stop pin 49 which there blocks further advance or withdrawal of two transverse stop formations 51a and 51b positioned across the clearance groove 51 at the circumferential groove 72 which is also located to ensure that the end 32a of the plunger 32 is positioned within the fluid chamber 14 for correctly metered volume aspiration of the pressure fluid therein. The fluid can be aspirated into the fluid chamber 14 by first unlocking the bayonet lock of the piston cap 24 and then forwardly moving the piston 18 so that it projects from the fluid chamber 14 and thus expands the open volume of the chamber. The volume expansion of the chamber produces a reduction in pressure which induces aspiration of the fluid from a fluid supply (not shown) through the piston bore 20 into the fluid chamber 14 as shown in FIG. 7. The piston can then be rearwardly withdrawn into the fluid chamber 14 as shown in FIG. 9, to displace some of the fluid and ensure that all air has been expelled. Thereafter, the piston is relocked and fluid coupler 22 can be connected to the balloon lead coupler 23 leading to the balloon B. If a 5 mm diameter balloon has been placed for example in an adult patient's lacrimal duct, the sleeve 36 and plunger 32 assembly can be rotated by the cap 44 to select the corresponding longitudinal groove 56 to be radially aligned with the latch hook 60 which has been removed from the notch 70 in the otherwise unnotched "prep" groove 55 (FIG. 2) to allow the selecting rotation. Upon alignment of the groove 56 with the latch hook 60, the corresponding indicia "5 mm" will be aligned with the arrow 76 (these corresponding alignments being radially 90° apart in the illustrated embodiment) and the lever 62 can be released to pivot the latch hook 60 into the lowermost notch 70 thereof along the circumferential groove 72 in order to lock the selection of groove 56.

Figure 13:
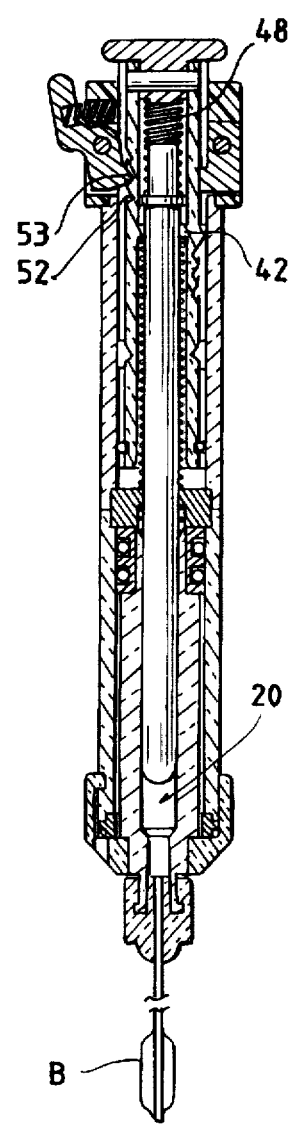
FIG. 13 is a sectional view similar to FIG. 12, showing sequential control sleeve advancement as well as compression of a pressure balance spring to balance pressure on the plunger.

To begin inflation of the balloon B, the cap 44 is manually depressed to forwardly displace the sleeve 36 and plunger 32 producing cammed release of the latch hook 60 from the notch 70 as the plunger 32 advances through the piston bore to begin pressurizing the fluid therein and deliver the pressurized fluid to begin inflation of the balloon B as shown in FIG. 12. As the sleeve notch 52 becomes aligned with and receives the spring biased insertion of the latch hook 60, the balloon B will have become partially inflated to approximately two atmosphere pressure, and this partial inflation will allow the physician to verify that the balloon is properly placed. Thereafter, as the cap and plunger 32 are further advanced to remove the catch hook 60 from the first notch 52 and then spring biased "snap" into the second notch 53 as shown in FIG. 13 (and ultimately into the third notch 54), the plunger advance will further pressurize and displace fluid to inflate the balloon B to a final pressure of, for example, approximately 8 atmosphere pressure. At this final pressure and balloon inflation, the preload force imposed by the accumulator spring 48 upon the plunger flange 50 and plunger 32 may be slightly exceeded by the inflating pressure in the balloon B, and therefore the spring 48 will yield and compress to allow the plunger 32 to slightly retract, as shown in FIG. 13, to enable a proper balancing of pressure on the plunger 32 and inflation of balloon B to the proper designated pressure level for dilation of the nasal lacrimal duct to correct epiphora. As the lacrimal duct expands under pressure from the balloon, the accumulator spring 48 slightly reexpands to maintain the predetermined pressure in the increased balloon volume.

Figure 14:
FIG. 14 is a sectional view similar to FIGS. 12 and 13 showing sequential retraction of the plunger and corresponding deflation of the connected balloon.

When the lacrimal duct dilation treatment has been completed, the release lever 62 is manually pivoted to unlatch the sleeve 36 allowing free expansion of the return spring 38 to drive the plunger 32 rearwardly in withdrawal from the piston bore 20, to the limit of retraction at which the "O-ring" cushion 80 impacts the guide stops 74 and the latch hook 60 as shown in FIG. 14. The terminal slots 82 in the sleeve 36 which are formed continuous with the circumferential groove seat for the O-ring cushion 80 permit the O-ring to slightly distort upon impact against the guide stop 74 and latch hook 60 additionally reducing the impact shock of the O-ring thereagainst. The resulting full retraction of the plunger from the piston bore 20 produces a lowered pressure therein which induces fluid drainage and deflation of the balloon B as shown in FIG. 14 to facilitate removal from the lacrimal duct upon completion of the dilation treatment.

While a preferred embodiment of the present invention is shown and described, it is envisioned that those skilled in the art may devise various modifications and equivalents without departing from the spirit and scope of the appended claims. For example, modified embodiments of the syringe structure in accordance with the invention can provide for control detent structure carried directly on the plunger structure in suitable modification.

The invention claimed is:

1. A syringe instrument having pressure control for particular use in medical balloon inflation procedures comprising:

a) a fluid chamber;

b) a plunger arranged to displace fluid from said chamber for delivery to inflate a medical balloon or the like; and, c) a control structure arranged to provide a series of releasable, spaced limits for respective displacements of said plunger within said chamber in order to pressurize said fluid at selective predetermined pressure levels governed by said limited plunger displacements, said control structure including detent structure arranged for releasable interference preventing displacement of said plunger from a respective one of said limits.

2. An instrument according to claim 1, wherein said detent structure comprises a plurality of stop formations in serial arrangement coupled to said plunger and a latch member releasably engageable with each said stop formation to define said plunger displacement limits.

3. An instrument according to claim 2, wherein said stop formations are defined by respective notches and said catch element is releasably insertable into said respective notches to retain said limited plunger displacements.

4. An instrument according to claim 1, further comprising plural arrangements of said spaced limits, differently spaced to provide said predetermined pressure levels in differently sequenced degrees of pressure for inflation of variably dimensioned medical balloons.

5. An instrument according to claim 4, wherein said plural arrangements of spaced limits are formed on a control member arranged for rotation relative to said fluid chamber for rotative selection of one of said plural arrangements.

6. An instrument according to claim 1, wherein said control structure comprises a control member coupled to said plunger to control displacement therewith relative to said fluid chamber.

7. An instrument according to claim 6, wherein said control member includes said series of releasible, spaced limits for said respective plunger displacements.

8. An instrument according to claim 6, wherein said plunger is disposed within a bore formed in said control member.

9. An instrument according to claim 6, further comprising coupling structure arranged to enable both relative movement as well as coupled displacement of said plunger and control member.

10. An instrument according to claim 9, wherein said coupling structure comprises a spring arranged between said plunger and control member.

11. An instrument according to claim 1, further comprising reverse drive structure for reverse-displacement of said plunger enabling serf-aspiration of fluid into the chamber, for deflation of said inflated balloon.

12. An instrument according to claim 11, wherein said reverse drive structure comprises a spring arranged to bias said plunger reverse-displacement.

13. An instrument according to claim 12, further comprising activation structure for activating said plunger reverse-displacement by said spring.

14. A syringe instrument having pressure control for particular use in medical balloon inflation procedures comprising:

a) a fluid chamber;
  b) a plunger arranged to displace fluid from said chamber for delivery to inflate a medical balloon or the like; and
  c) a control structure arranged to provide a series of releasable, spaced limits for respective displacements of said plunger within said chamber in order to pressurize said fluid at selective predetermined pressure levels governed by said limited plunger displacements, wherein said spaced limits are defined by respective notches and a catch element is releasably insertable into said respective notches to retain said limited plunger displacements; and
  d) reverse drive structure for reverse-displacement of said plunger enabling self-aspiration of fluid into the chamber, for deflation of said inflated balloon, and comprising a spring arranged to bias said plunger reverse-displacement and activation structure for activating said plunger reverse-displacement by said spring including a deflection structure arranged to enable manual withdrawal of said catch member from said detent notches.

15. An instrument according to claim 1, further comprising pressure balance mechanism cooperable with said plunger to enable pressure balance thereon in order to maintain a selective one of said predetermined pressure levels.

16. A syringe instrument having pressure control for particular use in medical balloon inflation procedures comprising:

a) a fluid chamber;
  a plunger arranged to displace fluid from said chamber for delivery to inflate a medical balloon or the like; and
  c) a control structure arranged to provide a series of releasable, spaced limits for respective displacements of said plunger within said chamber in order to pressurize said fluid at selective predetermined pressure levels governed by said limited plunger displacements, wherein said spaced limits are defined by respective notches and a catch element is releasably insertable into said respective notches to retain said limited plunger displacements; and
  d) pressure balance mechanism cooperable with said plunger to enable pressure balance thereon in order to maintain a selective one of said predetermined pressure levels, and including spring member bearing on said plunger and arranged to transmit drive force thereon to displace fluid from said chamber for said delivery.

17. An instrument according to claim 1, further comprising a displacement structure separate from said plunger, said displacement structure being reversibly displaceable into or from said chamber in order to enable charging aspiration of pressurizing fluid into said chamber (for subsequent pressurization by said plunger).

18. An instrument according to claim 17, wherein said displacement structure comprises a piston arranged for reciprocation relative to said chamber.

19. An instrument according to claim 18, wherein said piston comprises a through bore arranged in fluid communication with said chamber to enable both aspiration of said fluid therethrough into said chamber as well as displacement of said pressurizing fluid therethrough by said plunger displacements.

20. An instrument according to claim 19, wherein said piston through bore is arranged for reception of said plunger therethrough when said piston is displaced into said chamber.

21. An instrument according to claim 1, wherein said fluid chamber is arranged to enable insertion of said plunger from a first end thereof and a piston which reciprocates through a second end thereof.

22. An instrument according to claim 21, wherein said plunger and a piston are arranged for telescopic relation and displacement within said chamber.

23. An instrument according to claim 22, wherein said plunger is displaceable within a bore formed in said piston.

24. An syringe instrument for particular use in medical balloon inflation procedures comprising:

a) a fluid chamber;
  b) a plunger arranged to displace fluid from said chamber for delivery to inflate a medical balloon or the like; and
  c) reverse drive structure for reverse-displacement of said plunger enabling self-aspiration of fluid into said chamber, in order to deflate said inflated balloon, and comprising a spring arranged to bias said plunger reverse-displacement and activation structure for activating said plunger reverse-displacement by said spring, including a control detent structure arranged for releasible interference preventing displacement of said plunger.

* * * * *

UNITED STATES PATENT AND TRADEMARK OFFICE
CERTIFICATE OF CORRECTION

PATENT NO. : 5,634,910
DATED : June 3, 1997
INVENTOR(S) : Rowland W. Kanner, Richard M. Davis and Richard Rabenau It is certified that error appears in the above-indentified patent and that said Letters Patent is hereby corrected as shown below:

Column 7, Line 48 "a plunger" should be -- b) a plunger --

Signed and Sealed this

Sixteenth Day of September, 1997

*Attest:*

BRUCE LEHMAN

*Attesting Officer*     *Commissioner of Patents and Trademarks*